United States Patent [19]

Boyd

[11] Patent Number: 5,400,995

[45] Date of Patent: Mar. 28, 1995

[54] IV POLE WITH INTERIOR DRAG BRAKE

[75] Inventor: Howard Boyd, Oldenburg, Ind.

[73] Assignee: Hill-Rom Company, Inc., Batesville, Ind.

[21] Appl. No.: 869,001

[22] Filed: Apr. 15, 1992

[51] Int. Cl.⁶ .......................................... F16M 11/00
[52] U.S. Cl. .................................... 248/414; 248/407
[58] Field of Search ............... 248/414, 125, 407, 161, 248/600, 601, 619, 621

[56] References Cited

U.S. PATENT DOCUMENTS

| | | |
|---|---|---|
| D. 260,816 | 9/1981 | Zissimopoulos . |
| 383,815 | 5/1888 | Kilborn ........................ 248/414 |
| 1,290,809 | 1/1919 | Truax . |
| 1,490,650 | 4/1924 | Wagner . |
| 1,919,114 | 7/1933 | Ley ............................... 248/414 |
| 2,470,524 | 5/1949 | Scudder . |
| 2,673,771 | 3/1954 | Krewson . |
| 2,696,963 | 12/1954 | Shepherd . |
| 3,004,743 | 10/1961 | Wenger ........................ 248/414 |
| 3,153,123 | 10/1964 | Harman ........................ 248/414 |
| 3,552,577 | 1/1971 | Latham, Jr. . |
| 3,674,294 | 7/1972 | Kirkham .................... 248/414 X |
| 4,113,222 | 9/1978 | Frinzel ...................... 248/125 X |
| 4,225,104 | 9/1980 | Larson . |
| 4,262,872 | 4/1981 | Kodet . |
| 4,339,104 | 7/1982 | Weidman ..................... 248/407 |
| 4,360,184 | 11/1982 | Reid, III .................. 248/619 X |
| 4,511,157 | 4/1985 | Wilt, Jr. . |
| 4,511,158 | 4/1985 | Varga et al. . |
| 4,600,209 | 7/1986 | Kerr, Jr. . |
| 4,725,027 | 2/1988 | Bekanich . |
| 4,729,576 | 3/1988 | Roach . |
| 4,905,944 | 3/1990 | Jost et al. ..................... 248/125 |
| 4,945,592 | 8/1990 | Sims et al. . |
| 4,966,340 | 10/1990 | Hunter . |
| 4,993,683 | 2/1991 | Kreuzer . |
| 4,997,150 | 3/1991 | Mardollo ..................... 248/161 |
| 5,094,418 | 3/1992 | McBarnes, Jr. et al. . |
| 5,125,607 | 6/1992 | Pryor ............................ 248/125 |
| 5,141,210 | 8/1992 | Bauer et al. ............... 248/161 X |

Primary Examiner—Alvin C. Chin-Shue
Assistant Examiner—Korie H. Chan
Attorney, Agent, or Firm—Wood, Herron & Evans

[57] ABSTRACT

An IV pole having an interior drag brake which selectively prevents downward movement or allows downward movement of the pole due to gravitational acceleration including a first pole member and at least a second pole member which telescopes into and out of the first pole member. The second pole member includes on its lower end an O-ring encircling the end, and a nylon split collar encircling the O-ring. In another embodiment, a seal is disposed between the first and second pole members and is operable to create an air cushion beneath the second pole member and within the first pole member. The seal can be an O-ring seal, a Quad-Ring ® seal or a lip seal. A valve is disposed in the first pole member for bleeding off air between the first and second pole members, whereby the second pole member has a predetermined or selectively controllable rate of descent with respect to the first pole member.

12 Claims, 2 Drawing Sheets

IV POLE WITH INTERIOR DRAG BRAKE

FIELD OF THE INVENTION

This invention relates to IV poles, and more particularly to an IV pole including an interior drag brake therein for selectively preventing free fall or allowing a controlled rate of descent of the pole and IV bags supported thereby due to gravitational acceleration.

BACKGROUND OF THE INVENTION

IV poles currently in existence have two or more pole sections which telescope to provide for height adjustment of bags of IV solution supported by the IV pole. Typically the outer pole includes a spring loaded pin mechanism which fits into one of several detents in the inner telescoping pole. When the spring loaded pin is retracted from the detent, the inner telescoping pole can be adjusted manually downwardly or upwardly as desired.

A disadvantage with IV poles as they presently exist is that when the detent pin is released, it is possible for the inner telescoping pole to immediately fall to the bottom of the outer pole due to the weight of the bags of IV solution suspended upon the inner pole. This free fall phenomenon due to gravitational acceleration is objectionable and thus subject to criticism.

It has therefore been an objective of the present invention to provide an IV pole which will have sufficient drag as to not freely fall under the weight of bags of IV solution supported by the pole upon releasing its detent pin mechanism.

It has been another objective of the present invention to provide an IV pole which has a variable drag so as to have a controllable rate of fall under the weight of bags of IV solution supported by the pole.

SUMMARY OF THE INVENTION

These objectives are achieved by the present invention by providing an IV pole that includes an interior drag brake which selectively prevents downward movement or allows downward movement of the pole and associated bags of IV solution due to gravitational acceleration.

The IV pole includes a first pole member, and at least a second pole member which telescopes into and out of the first pole member. The second pole member includes on its lower end an O-ring encircling the end, and a nylon split collar encircling the O-ring. The nylon split collar generates a sufficient frictional force against the inner diameter of the first pole member such that the second pole member will not move downwardly with respect to the first pole member under the weight of the bags of solution supported by the second pole member, or alternatively a sufficient frictional force so as to cause the second pole member to move downwardly with a predetermined controlled rate of descent.

The nylon split collar is urged against the inner diameter of the first pole member by the O-ring, thus preventing the nylon split collar from taking a permanent set which would cause it to lose its holding efficiency over time.

The interior drag brake is a spool having a circumferential groove, an O-ring disposed in the groove, and a nylon split collar encircling the O-ring. The spool is adapted to be secured to the end of a tube or rod. The depth of the groove can be varied to completely prevent free fall, or to allow a controlled rate of descent of the pole.

In another embodiment, the IV pole comprises a first pole member, at least a second pole member operable to telescope into and out of the first pole member, a seal disposed between the first and second pole members and operable to create an air cushion beneath the second pole member and within the first pole member, and a valve disposed in the first pole member for bleeding off air between the first and second pole members, whereby the second pole member has a predetermined or selectively controllable rate of descent with respect to the first pole member. The seal can be either an O-ring seal, a Quad-Ring ® seal or a lip seal, and the valve is preferably a needle valve.

One advantage of the present invention is that an IV pole is provided which will not freely fall under the weight of bags of solution supported by the pole when the pole is released by its detent pin mechanism.

Another advantage of the present invention is that an IV pole has been provided which incorporates a variable interior drag brake therein thereby providing a controlled rate of fall of the pole under the weight of bags of IV solution.

Yet another advantage of the present invention is that an IV pole has been provided which incorporates an interior drag brake therein, which drag brake has a predictable holding efficiency and operation over a long period of time.

These and other objectives and advantages of the present invention will become more readily apparent during the following detailed description taken in conjunction with the drawings herein, in which:

DESCRIPTION OF THE PREFERRED EMBODIMENT

Figure 1:
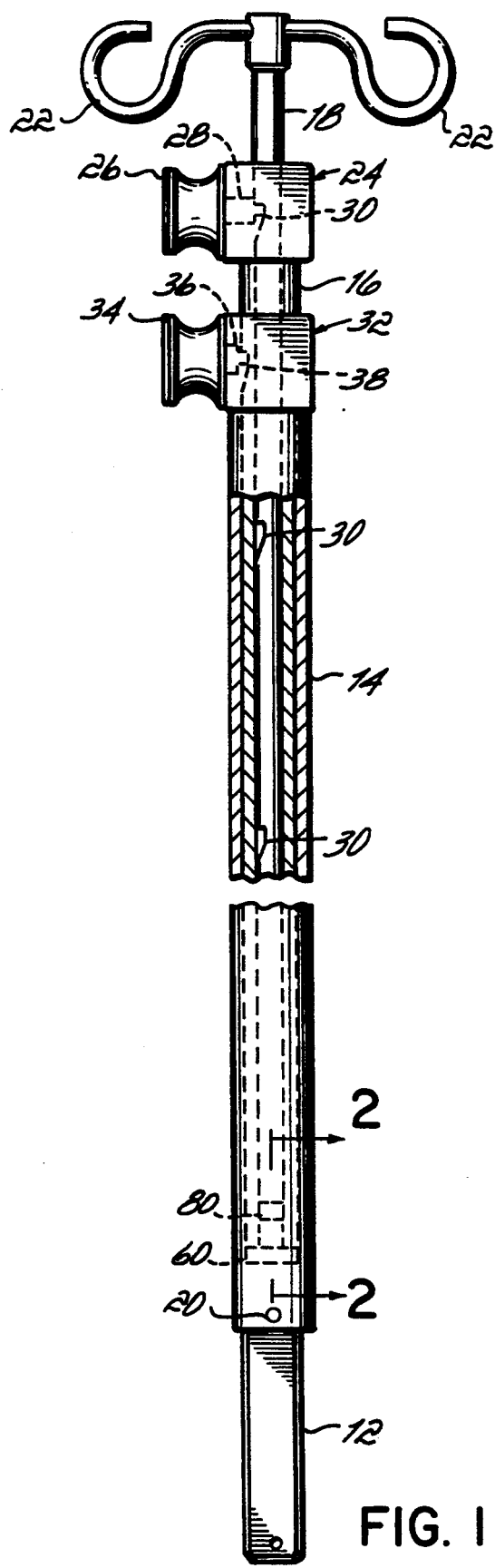
FIG. 1 is a side elevational view, partially broken away, of the IV pole of the present invention.

With reference to FIG. 1, there is illustrated an IV pole 10 of the present invention. The IV pole 10 includes an extension 12, a lower pole or tube 14, an upper pole or tube 16, and a pole or rod 18. Rod 18 is operable to telescope into and out of the upper tube 16, while the upper tube 16 is operable to telescope into and out of the lower tube 14. Lower tube 14 telescopes up and down upon the extension 12, but is generally permanently located after adjustment as by pinning the lower tube 14 to the extension 12 via pin 20.

The rod 18 includes hooks 22 for supporting one or more bags of IV solution (not shown) thereon. An upper bushing assembly 24 is mounted to the upper end of the upper tube 16 and includes a knob 26 for manipulating a spring loaded pin 28. The pin 28 is receivable into one of a number of detents 30 spaced along the length of the extension rod 18. Similarly, a lower bushing assembly 32 is mounted to the upper end of the lower tube 14 and includes a knob 34 which is used to withdraw a spring loaded pin 36 from one or more detents 38 along the length of the upper tube 16.

Figure 2:
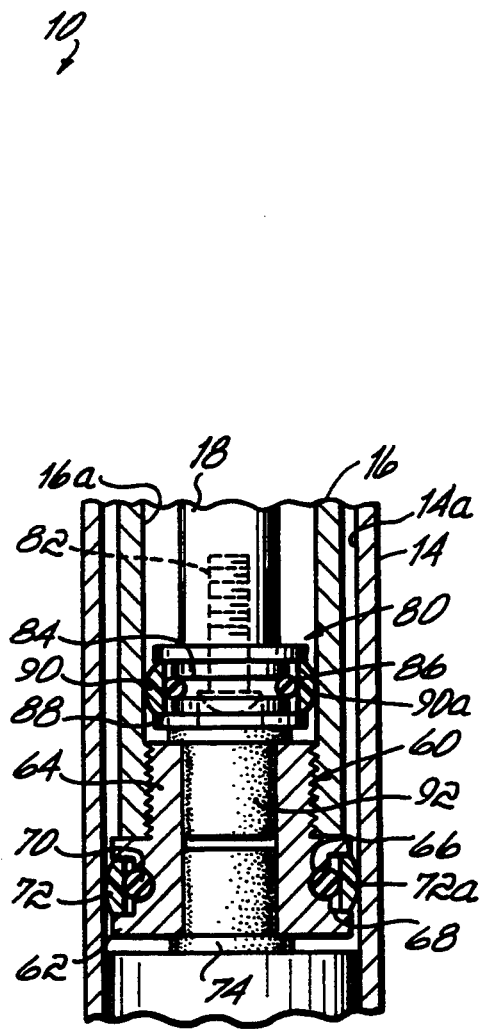
FIG. 2 is a cross-sectional view taken along lines 2—2 of FIG. 1.

Referring now to FIG. 2, the rod 18, upper tube 16 and lower tube 14 are shown in cross-section, and specifically illustrating the lower ends of rod 18 and upper tube 16. The upper tube 16 has a threaded spool 60 threaded into its lower end. The threaded spool 60 includes a spool portion 62 and a threaded stud portion 64 which threads into the lower end of the upper tube 16. The spool portion 62 includes a diametrically innermost circumferential groove 66 and a diametrically outermost circumferential groove 68 generally wider than the groove 66. The inner groove 66 locates a rubber O-ring 70 therein. The outermost groove 68 locates a nylon split collar 72 therein, the outermost portion 72a of which is urged into contact with the inner diameter 14a of the lower tube 14 by the resiliency of the nylon collar and by the O-ring 70. The spool portion 62 could employ only a single groove with the O-ring 70 disposed therein and the split collar 72 encircling the O-ring 70. Additionally other resilient materials other than nylon can be used for collar 72, for example plastics, etc., with satisfactory results. Therefore the invention is not to be limited to any particular material. Moreover, should it be desired, the collar 72 could be eliminated with the invention employing an O-ring 70 of proper cross-sectional diameter to effect proper friction between O-ring and inner tube diameter. Conversely the O-ring could be eliminated with the invention employing a collar of proper cross-section for frictional purposes. A rubber bumper plug 74 is press fitted into the lower side of the threaded spool 60 to prevent any metal-to-metal contact upon lowering the upper tube 16.

The rod 18 includes on its lower end a spool 80 which is secured to the rod 18 via a cap screw 82 which is counter-sunk into the spool 80. The spool 80 includes a diametrically innermost circumferential groove 84 which contains an O-ring 86, and a diametrically outermost circumferential groove 88 generally wider than the groove 84 which contains a nylon split collar 90. As with threaded spool 60, spool 80 could employ only a single groove as well. The O-ring 86 urges the outermost portion 90a of the nylon split collar 90 outwardly against the inner diameter 16a of the upper tube 16. A rubber plug 92 is press fitted into the upper end of the threaded spool 60 to prevent metal-to-metal contact between the spool 80 and the threaded portion 64 of spool 60.

In use, knob 26 is pulled outwardly thereby pulling pin 28 against the spring force and free of detent 30. Extension rod 18 remains in its original vertical position, however, as the nylon split collar 90 bearing against the inner diameter 16a of the upper tube 16 prevents the rod 18 from moving downwardly under the influence of the weight of bags of IV solution supported thereon. Rod 18 may be grasped and moved either upwardly or downwardly with ease, however, as the frictional force generated by the split collar 90 is not so great as to be difficult to overcome. Split collar 72 and O-ring 70 function in much the same manner for raising and lowering the upper tube 16 with respect to the tube 14 and for preventing undesired gravity-induced movement therebetween.

Grooves 66 and 84 can be modified to selectively control the friction force between collar 72 and tube 14, and collar 90 and tube 16, respectively. For example, the deeper the grooves the less friction generated and the shallower the grooves the more friction generated. Consequently, if a slow free fall is desired, the rate of descent can be selectively adjusted and controlled.

Figure 3:
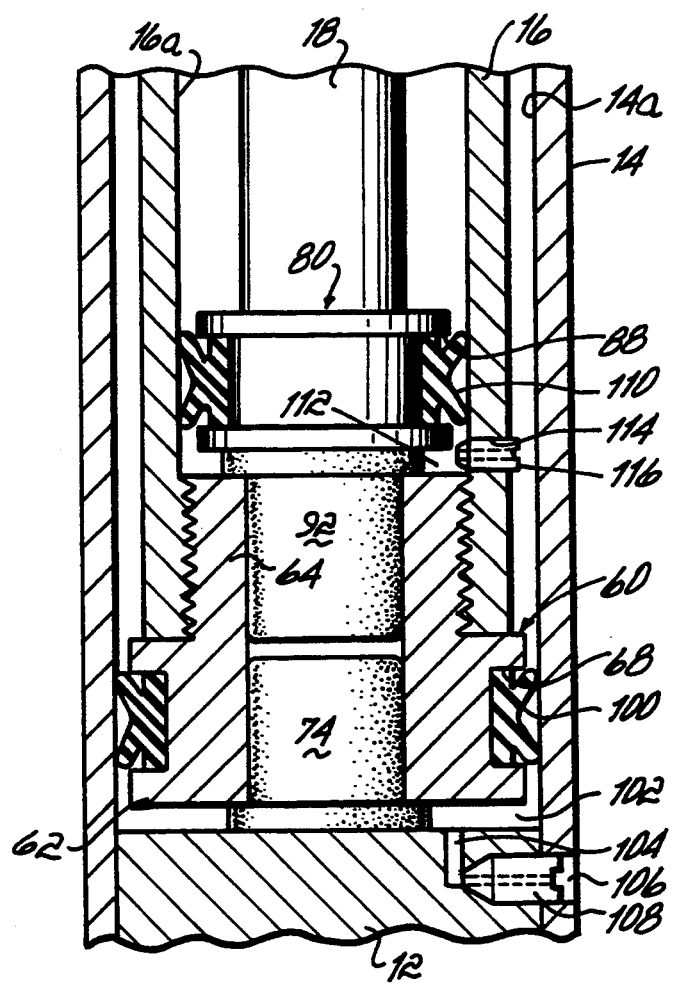
FIG. 3 is a view similar to FIG. 2 illustrating another embodiment of the present invention.

Referring now to FIG. 3, and with like numbers representing like components, an alternative embodiment of the present invention is illustrated. A four lobed Quad-Ring ® seal 100 (registered trademark of and manufactured by Minnesota Rubber and Gasket Company, Minneapolis, Minn.) is disposed in groove 68 of spool 60 and provides a seal between spool 60 and surface 14a of tube 14. An air pocket or cushion 102 is thus formed beneath tube 16 and between tubes 14 and 16. An air passage 104 is located in extension 12 and connects with an air passage 106 in tube 14. A needle valve 108 is disposed in the passage 106 and is adjustable to provide for a selective rate of bleeding off of air from air cushion 102, thereby providing a controlled rate of descent of tube 16 and rod 18 with respect to tube 14.

Similarly, spool 80 has disposed in groove 88 a Quad-Ring ® seal 110 for engaging surface 16a of tube 16. There is thereby created an air cushion 112 beneath rod 18 and within tube 16. Tube 16 includes a passage 114 which communicates with air cushion 112. A needle valve 116 is disposed in the passage 114 and is operable to bleed off air from the air cushion 112, thereby providing for a controlled rate of descent of rod 18 with respect to tube 16.

Figure 4A:
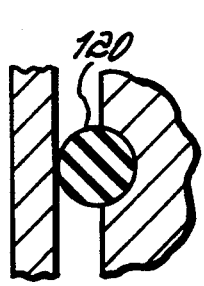
FIG. 4A is an enlarged view of a O-ring seal used in conjunction with the invention of FIG. 3.
Figure 4B:
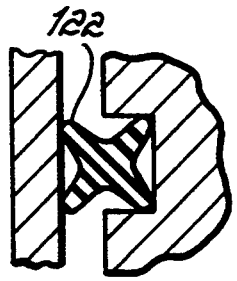
FIG. 4B is a view similar to FIG. 4A illustrating a Quad-ring seal.
Figure 4C:
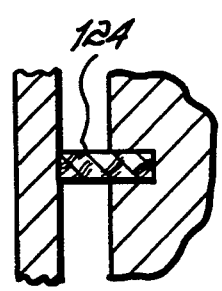
FIG. 4C is a view similar to FIGS. 4A–B illustrating a lip seal.

With reference to FIGS. 4A–C, it will be seen that numerous types of seals may be employed between the telescoping poles or rods of an IV pole to provide for sealing to enable the telescoping member to ride downwardly atop an air cushion. For example, in FIG. 4A, a simple O-ring seal 120 is illustrated. In FIG. 4B, the before mentioned four lobed Quad-Ring ® seal 122 is illustrated, and finally in FIG. 4C, a lip seal 124 is illustrated, which could be either rubber as in the O-ring and Quad-Ring ® seals of FIGS. 4A and 4B, respectively, or felt.

Those skilled in the art will readily recognize numerous adaptations and modifications which can be made to the present invention and which will result in an improved IV pole with interior drag brake, yet without departing from the spirit and scope of the present invention, as all of which will be encompassed by the appended claims and their equivalents. Accordingly, I intend to be limited only by the claims and their equivalents.

What is claimed is:

1. An IV pole comprising:

a first IV pole member;

at least a second IV pole member operable to telescope into and out of said first pole member, said second pole member including means mounted on an upper end thereof for supporting IV fluid bags thereon; and means mounted on one of said first and second pole members for providing a drag brake to selectively prevent downward movement or allow controlled downward movement due to gravitational acceleration of said second pole member and any IV bags supported thereon;

said means for providing a drag brake comprising a ring of a first stiffness encircling said second pole member and a collar of a second stiffness encircling said ring, said second stiffness being greater than said first stiffness, the resilience of said ring forcing said collar against said first pole member and preventing said collar from taking a permanent set.

2. The IV pole of claim 1 wherein said drag brake means comprises an O-ring encircling said second pole member and a nylon split collar encircling said O-ring.

3. An IV pole comprising:

a first tubular IV pole;

a second tubular IV pole operable to telescope into and out of said first tubular pole; and an IV rod operable to telescope into and out of said second tubular pole and including means mounted on an upper end thereof adapted to support one or more bags of IV solution thereon;

said second pole and rod each having on respective lower ends thereof a ring of a first stiffness and a collar of a second stiffness encircling said ring, said second stiffness being greater than said first stiffness, the resilience of said ring forcing said collar against said first pole and preventing said collar from taking a permanent set, said rings and collars being operable to selectively prevent free fall or allow controlled downward movement of said second pole and rod and any IV bags supported thereon due to gravitational acceleration.

4. The IV pole of claim 3 wherein said collars are formed of a plastic.

5. The IV pole of claim 3 wherein said collars are formed of nylon.

6. The IV pole of claim 3 wherein said rings are formed of rubber.

7. An IV pole comprising:

a first tubular pole;

a second tubular pole operable to telescope into and out of said first tubular pole; and a rod operable to telescope into and out of said second tubular pole and adapted to support one or more bags of IV solution thereon;

said second pole and rod each having on respective lower ends thereof an interior drag brake comprising:

a spool having a circumferential groove therein;

a ring of a first stiffness disposed in said groove and encircling said spool; and a collar of a second stiffness greater than said first stiffness encircling said ring, each said collar having an outer diameter friction surface associated therewith, each said ring being operable to urge each said friction surface against a surface of said first and second poles, respectively, in frictional relation thereto and to prevent said collars from taking a permanent set.

8. An IV pole comprising:

a first IV pole member;

at least a second IV pole member operable to telescope into and out of said first pole member, said second pole member including means mounted on an upper end thereof for supporting IV fluid bags thereon;

seal means disposed between said first and second pole members and operable to create an air cushion beneath said second pole member and within said first pole member; and an adjustable valve means for selective and controlled bleeding off of air between said first and second pole members;

whereby said second pole member and any IV fluid bags supported thereby have a predetermined rate of descent with respect to said first pole member due to said adjustable valve.

9. The IV pole of claim 8 wherein said seal means is an O-ring seal.

10. The IV pole of claim 8 wherein said seal means is a four lobed ring seal.

11. The IV pole of claim 8 wherein said seal means is a lip seal.

12. The IV pole of claim 8 wherein said valve means is a needle valve.

* * * * *